United States Patent
Konstorum et al.

(10) Patent No.: US 6,749,560 B1
(45) Date of Patent: *Jun. 15, 2004

(54) ENDOSCOPE SHAFT WITH SLOTTED TUBE

(75) Inventors: Gregory S. Konstorum, Stamford, CT (US); Edward A. Grabover, Danbury, CT (US)

(73) Assignee: Circon Corporation, Southborough, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/427,164

(22) Filed: Oct. 26, 1999

(51) Int. Cl.[7] ............................................. A61B 1/005
(52) U.S. Cl. ........................ 600/143; 600/139; 604/525; 604/530
(58) Field of Search ................................ 600/139–143; 604/95.01, 95.04, 95.05, 525, 530

(56) References Cited

U.S. PATENT DOCUMENTS

| | | | |
|---|---|---|---|
| 4,409,457 A | * 10/1983 | Takahashi et al. | ....... 219/69.17 |
| 4,580,551 A | 4/1986 | Siegmund et al. | |
| 4,802,461 A | 2/1989 | Cho | |
| 5,178,129 A | * 1/1993 | Chikama et al. | ............. 600/142 |
| 5,325,845 A | 7/1994 | Adair | |
| 5,334,145 A | * 8/1994 | Lundquist et al. | ........ 604/95.04 |
| 5,381,782 A | * 1/1995 | DeLaRama et al. | ...... 604/95.01 |
| 5,483,951 A | 1/1996 | Frassica et al. | .............. 600/104 |
| 5,681,263 A | 10/1997 | Flesch | ........................ 600/141 |
| 5,873,817 A | 2/1999 | Kokish et al. | ............... 600/143 |
| 5,873,906 A | * 2/1999 | Lau et al. | .................... 128/898 |
| 5,938,588 A | 8/1999 | Grabover et al. | ........... 600/150 |
| 6,012,494 A | * 1/2000 | Balazs | ......................... 138/110 |
| 6,171,316 B1 | * 1/2001 | Kovac et al. | ................ 606/144 |

FOREIGN PATENT DOCUMENTS

| | | | |
|---|---|---|---|
| GB | 2 130 885 A | | 6/1984 |
| JP | 09-024019 A | * | 1/1997 |

* cited by examiner

*Primary Examiner*—John P. Leubecker
(74) *Attorney, Agent, or Firm*—Harrington & Smith, LLP

(57) ABSTRACT

An endoscope comprising a control section and a shaft extending from the control section. The shaft has a frame with a one-piece tube along a majority of a length of the shaft. The tube comprises a superelastic alloy and slots into the tube along at least one-section of the tube. Superelastic properties of the superelastic alloy allow the tube to bend proximate the slots without substantial permanent deformation of the tube. The superelastic alloy provides the shaft with adequate stiffness and torque resistance to be inserted into a patient's body.

12 Claims, 5 Drawing Sheets

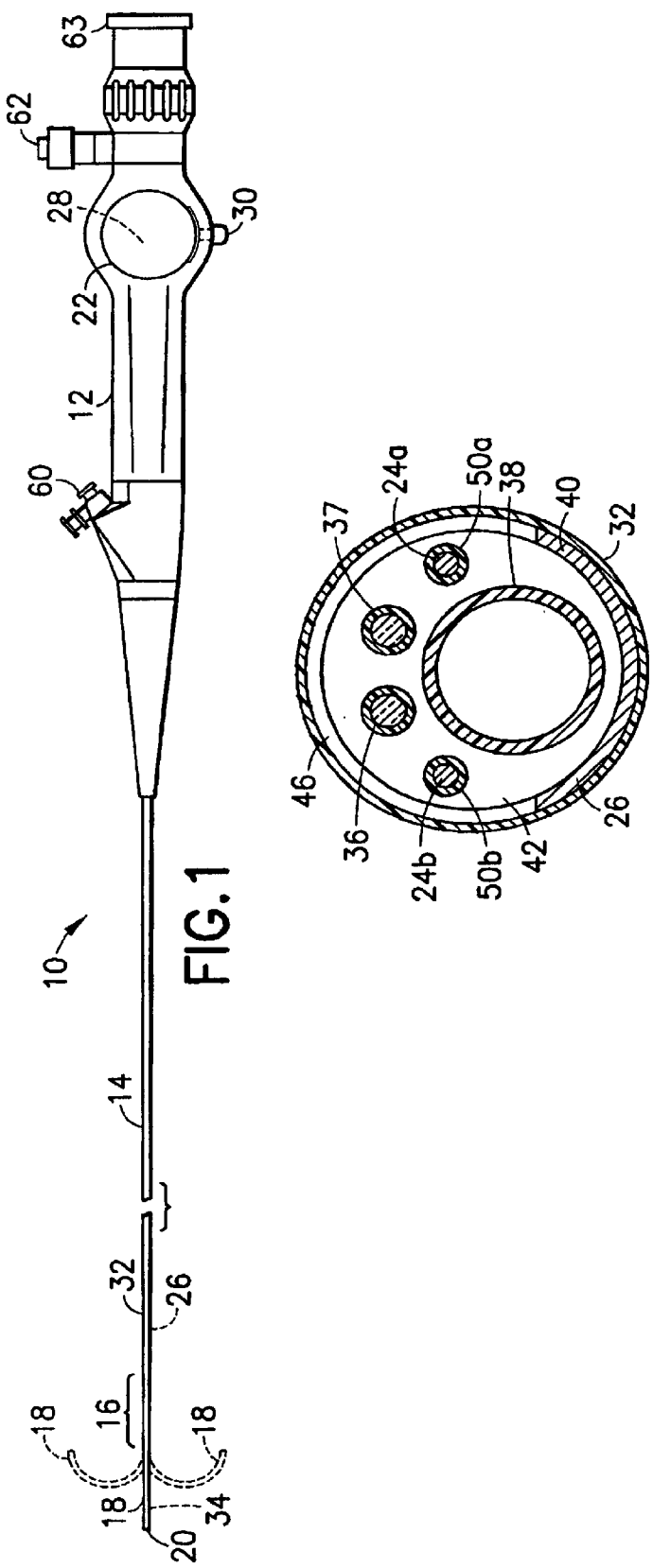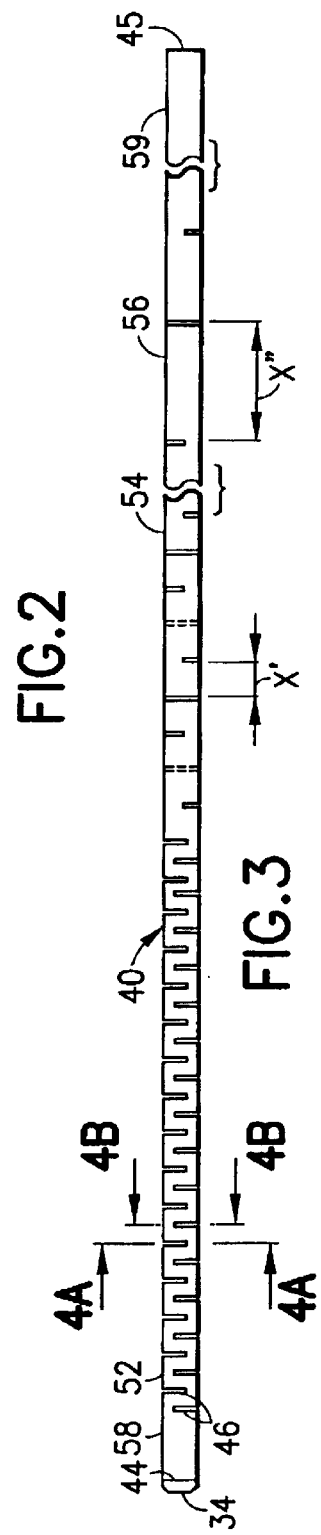

ENDOSCOPE SHAFT WITH SLOTTED TUBE

BACKGROUND OF THE INVENTION

1. Field of the Invention

The present invention relates to medical instruments and, more particularly, to an endoscope.

2. Prior Art

U.K. Patent Application No. 2130885 discloses a flexible distal end portion for an endoscope. The end portion is made from plastic material with vertebrae connected by an elongate member or spine. U.S. Pat. No. 5,938,588 discloses an endoscope with wire sheaths made as solid tubes from a superelastic alloy material.

SUMMARY OF THE INVENTION

In accordance with one embodiment of the present invention, an endoscope is provided comprising a control section and a shaft extending from the control section. The shaft has a frame with a one-piece tube along a majority of a length of the shaft. The tube comprises a superelastic alloy and slots into the tube along at least one section of the tube. Superelastic properties of the superelastic alloy allow the tube to bend proximate the slots without substantial permanent deformation of the tube. The superelastic alloy provides the shaft with adequate column strength, flexibility and torque resistance to be inserted into a patient's body.

In accordance with another embodiment of the present invention, an endoscope is provided comprising a shaft, a fiber optic system and the working channel passing through the shaft, and a deflection control system passing through the shaft. The shaft includes a frame comprising a tube of superelastic material with slots into the tube. The slots extend into the, tube in at least two different directions.

In accordance with another embodiment of the present invention, an endoscope is provided comprising a control section; and a shaft extending from the control section. The shaft comprises a general tube shaped frame member. The shaft comprises a substantially uniform outer dimension along substantially an entire length of the shaft. The tube shaped frame member provides the shaft with at least two sections along the length of the shaft having two different flexibilities (stiffnesses).

In accordance with one method of the present invention, a method of manufacturing an endoscope shaft frame is provided comprising steps of providing a tube of superelastic alloy; and making slots into the tube to form at least one section of the tube with an increased flexibility.

In accordance with another method of the present invention, a method of manufacturing endoscopes is provided comprising steps of providing a first type of shaft frame comprising a first tube with a first pattern of slots into the first tube; providing a second type of shaft frame comprising a second tube with a second pattern of slots into the second tube, the second pattern, being different than the first pattern; and assembling a first one of the endoscopes with the first type of shaft frame and a second one of the endoscopes with the second type of shaft frame. The first and second endoscopes comprise different flexibility, torque resistance and column strength patterns along their lengths provided by the different patterns of slots in the first and second tubes.

BRIEF DESCRIPTION OF THE DRAWINGS

The foregoing aspects and other features of the present invention are explained in the following description, taken in connection with the accompanying drawings, wherein:

FIG. 1 is a side elevational view of an endoscope incorporating features of the present invention;

FIG. 2 is a cross-sectional view of the shaft of the endoscope shown in FIG. 1;

FIG. 3 is a side elevational view of the tube used for the frame of the shaft shown in FIG. 2;

DETAILED DESCRIPTION OF THE PREFERRED EMBODIMENT

Figure 4A:
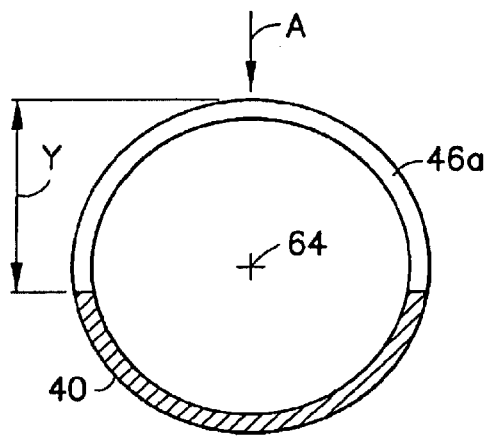
FIG. 4A is a cross-sectional view of the tube shown in FIG. 3 taken along line 4A—4A.

Referring to FIG. 1, there is shown a side elevational view of an endoscope 10 incorporating features of the present invention. Although the present invention will be described with reference to the embodiments shown in the drawings, it should be understood that the present invention can be embodied in many alternate forms of embodiments. In addition, any suitable size, shape or type of elements or materials could be used.

The endoscope 10 generally comprises a handle or control 12 and a flexible or semi-flexibile shaft 14 connected to the handle 12. The shaft 14 includes a passive deflection section 16 and an active deflection section 18 at the distal end of the shaft 14. A control system 22 to control the active deflection section 18 extends from the handle 12 to the active deflection section 18. Referring also to FIG. 2, the control system 22 generally comprises a pair of control wires 24a, 24b, two wire sheaths 50a, 50b, and an actuator 28. The wires 24a, 24b are connected to the actuator 28 at one end and are connected to the active deflection section 18 at a second end.

In the preferred embodiment, the handle 12 has a user operated slide or lever 30. The lever 30 is connected to the actuator 28. The actuator 28 is adapted to pull and release the two wires 24a, 24b of the control system 22. When the lever 30 is moved by the user, the actuator 28 is moved. The actuator 28 may be a drum or pulley rotatably connected to the handle 12 to pull one wire 24a, 24b while releasing the other. In an alternate embodiment, the actuator may be any suitable type of device, such as a rocker arm adapted to pull and release the wires of the control system 22. In another alternate embodiment, where the control system may have two or more pairs of control wires, the handle will have additional actuators and corresponding controls to drive the additional pairs of control wires. In still other alternate embodiments, the handle may have knobs with rack and pinion mechanisms or other suitable user operated controls for the control system.

The shaft 14 is cantilevered from the handle 12. In the preferred embodiment, the flexible shaft 14 has about an 8 Fr diameter. In alternate embodiments, the flexible shaft could have any suitable diameter. The flexible shaft 14 includes the control wires 24a, 24b of the control system 22, a fiber optical image bundle 37, a fiber optical illumination bundle 36, and a working channel 38. A port 60 for inserting instruments (not shown) into the channel 38 is located on the handle 12. The handle 12 also has a light source post 62 for connecting a light source (not shown) to the illumination bundle 36. In addition, the handle 12 has an eyepiece 63 for a user to view an image transmitted by the image bundle 37 from the front end 20. In alternate embodiments, the flexible shaft may house different systems within. The shaft 14 generally comprises a frame 26, a cover 32 and an objective head 34. Referring also to FIG. 3, the frame 26 generally comprises a one-piece tube 40. However, in alternate embodiments the frame could be comprised of more than one tube, such as multiple tubes connected in series, and could comprise additional members. The tube 40 is preferably comprised of a shape memory alloy material, such as Tinel or Nitinol. The shape memory alloy material is used for its superelastic properties exhibited by the material's ability to deflect and resiliently return to its natural or predetermined position even when material strains approach 4%, or an order of magnitude greater than the typical yield strain of 0.4% giving rise to plastic deformation in common metals. Thus, the term "superelastic alloy" is used to denote this type of material. The wire sheaths 50a, 50b may also be comprised of this type of material such as disclosed in U.S. Pat. No. 5,938,588 which is hereby incorporated by reference in its entirety.

The tube 40 has a center channel 42 with open front and rear ends 44, 45, and slots 46 along at least part of its length. In this embodiment the slots have different patterns along different sections or lengths of the tube. More specifically, in this embodiment the slots 46, are configured into three sections 52, 54, 56. Each section has a different pattern of the slots 46. The pattern(s) of the slots 46 can be configured based upon, for example, the following variables:

distance or spacing between adjacent slots;

direction(s) of the slots into the tube 40;

depth of the slots into the tube;

width of the slots;

shape of the slots; and intermixing of different directions of the slots along a length of the tube.

In alternate embodiments the tube 40 could have more or less than three sections of different slot patterns, such as only one or two. In addition, rather than abrupt transitions between sections of different slot patterns, the tube could be provided with gradual or intermixed slot transition zones between sections. In this embodiment the tube 40 also has two sections 58, 59 which do not have slots therein.

Figure 4B:
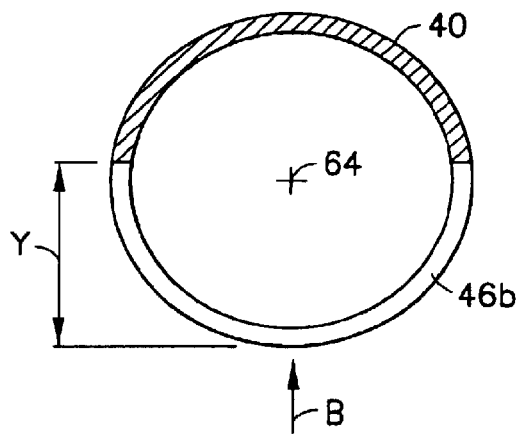
FIG. 4B is a cross-sectional view of the tube shown in FIG. 3 taken along line 4B—4B.
Figure 4C:
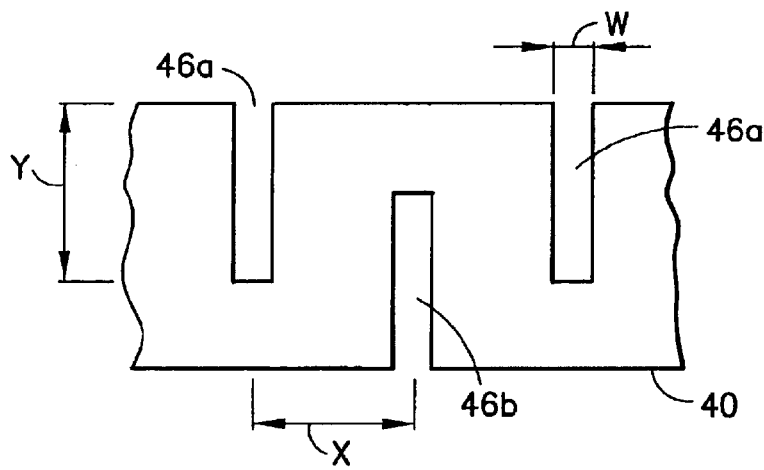
FIG. 4C is an enlarged view of a portion of the first section of the tube shown in FIG. 3.
Figure 5:
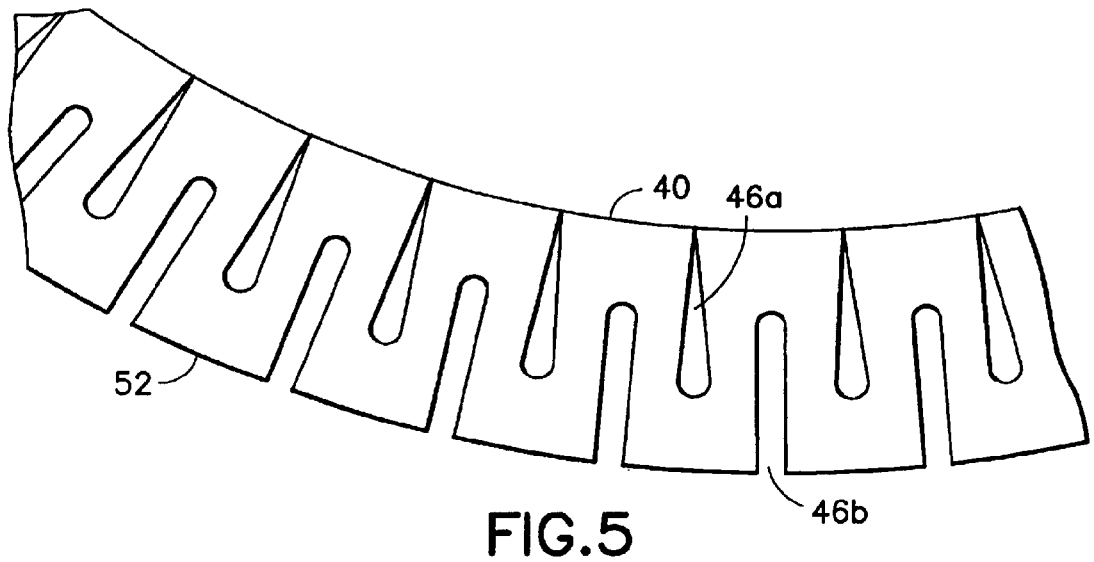
FIG. 5 is a partial side elevational view of the tube shown in FIG. 3 being bent.

Referring also to FIGS. 4A and 4B, the first section 52 of the slots 46 is provided along the length of the active deflection section 18 of the shaft. In this embodiment the active deflection section 18 is two-way deflectable as shown by dotted lines in FIG. 1. In alternate embodiments the active deflection section 18 could be merely one-way deflectable or more than two way deflectable. With the two way active deflection section 18 the frame is provided with two slot directions A and B into the side of the tube 40 which are 180° offset from each other. Referring also to FIG. 4C, the slots 46 have a depth Y into the tube 40, but in opposite directions for the two types of slots 46a, 46b relative to the center axis 64 of the tube 40. The slots have a centerline spacing X between adjacent slots 46a, 46b. The slots 46a, 46b have a width W. In this embodiment the values for W, X and Y are the same along the length of the first section 52. However, in alternate embodiments they could vary. Referring also to FIG. 5, a portion of the first section 52 is shown in a bent shape. The slots 46 provide the tube 40 with increased flexibility along the length of the first section 52. In addition, the two directions A, B of the slots 46 in the first section 52 limit this increased flexibility to two opposite directions. The first section could have slots in only one direction for limited increased flexibility in only one direction or slots in four or more directions for four-way or omni-directional increased flexibility.

Referring to FIGS. 3 and 6a–6d the second section 54 is provided along the length of the passive deflection section 16 (see FIG. 1). However, the passive deflection section 16 need not have slots 46 in its length of the frame. In this embodiment the tube 40 is provided with slots 46a, 46b, 46c and 46d into the tube 40 in four directions A, B, C and D which are offset 90° from each other. The slots 46a, 46b, 46c, 46d are arranged in series in a repeating pattern, but any suitable intermixing of the pattern of the slots 46a, 46b, 46c, 46d could be provided. In this embodiment the distance X' between adjacent slots 46 in the second section 54 is larger than the distance X between adjacent slots 46 in the first section 52. However, any suitable spacing(s) could be provided for X' including different spacings for X' along the length of the second section 54. Also in this embodiment the depth Y' of the slots 46a, 46b, 46c and 46d in the second section 54 are less than depth Y in the first section 52. In this embodiment the depth Y' is about ½ the diameter of the tube 40 and the depth Y is about ⅔ the diameter of the tube 40. However, Y and Y' could have any suitable depths. In addition, Y' could be different in different ones of the slots 46a, 46b, 46c, 46d along the length of the second section 54, such as deeper towards the front of the tube. The widths of the slots 46a, 46b, 46c and 46d along the second section 54 could be the same as W for the first section 54, could be different from the width W for the first section 52, and/or could vary or be different along the length of the second section 54, such as wider towards the front of the tube. The second section 54, preferably has a larger column strength, larger stiffness (or less flexibility), and larger torque stability suitable for passive deflection rather than active deflection as the first section 52. By providing the slots further apart from each other and with a shallower depth Y', the second section 54 has a stronger column strength and torque stability than the first section 52. The four directions A, B, C, D of the slots also provide four way deflection capability for the second section 54, rather than merely two way deflection as in the first section, for better passive deflection capabilities.

The third section 56 of the tube 40 is provided between the second section 54 and the rear end non-slotted section 59. However, in an alternate embodiment the third section need not have slots. In this embodiment the third section 56 extends along a majority of the length of the tube 40. The pattern of slots 46 along the third section 56 has a different spacing X", but is otherwise the same as the pattern of slots in the second section 54. In an alternate embodiment the Y and W variables could be different, the directions of the slots 46 in the third section 56 could be different, and the distance X" could vary along the length of the third section. FIGS. 7A–7E show one such variation wherein the third section 56' of the tube 40 has slots 46 in five directions M, N, O, P, Q into the tube. The third section preferably has a higher column strength, stronger stiffness (or less flexibility), and stronger torque stability than the first and second sections 52, 54. In this embodiment this is provided by providing the larger distance X", but could alternatively be provided by any one or combination of the other variables that would effect column strength and torque stability. In the embodiment when the third section 56 does not have slots, the thickness of the wall of the tube would be selected to provide sufficient shaft flexibility without use of slots. Section 59 extends into the handle 12 and is fixedly connected to the frame of the handle.

Referring back to FIGS. 1–3, the cover 32 is preferably comprised of a resilient plastic or polymer material. The cover could also include a structural reinforcement, such as disclosed in U.S. patent application Ser. No. 09/087,305 filed May 29, 1998 entitled "Flexible Pressure Resistant Cover For The Articulation System Of A Medical Instrument" which is hereby incorporated by reference in its entirety. The cover 32 is preferably directly attached to the tube 40, but not by adhesive. However, in alternate embodiments any suitable means could be used to attach the cover 32 to the tube 40 including use of adhesive. The cover 32 can be attached along the entire length of the tube 40 or can be attached at predetermined limited locations, such as being merely attached at sections 58, 59 and not attached anywhere else. Therefore, there may be lengths along the shaft 14 where the cover is able to move relative to the tube 40. In the prior art adhesive was used in different thicknesses along the length of the shaft to provide different column strengths and shaft flexibility along the length of the shaft. A thicker amount of adhesive was used towards the rear of the shaft to make the column strength of the shaft stronger or stiffer at the rear of the shaft, but with the undesired problem that the rear of the shaft had a larger outer diameter than the front of the shaft. It is preferable to have a small outer diameter, such as when the endoscope is inserted through small apertures such as a patient's ureter or urethra. With the present invention, because the tube 40 provides sufficient column strength and stiffness, there is no need to increase column strength and stiffness by use of increased thickness of adhesive. Therefore, the shaft 14 can have a uniform outer diameter along its length. Thus, the thickness or outer dimension of the shaft is minimized.

In the prior art the objective head was attached to a deflection assembly and the deflection assembly was attached to a shaft assembly. The present invention allows an endoscope to be provided which does not have a separate active deflection assembly and a separate shaft assembly. Instead, the present invention allows the tube 40 to extend the entire length of the shaft with the single tube 40 performing functions that were previously preformed by the two assemblies in the prior art. By use of the single tube 40 the shaft 14 can be manufactured and assembled in less time and with less cost than in the prior art two assembly shaft and, can be more reliable because less parts are used, the superelastic alloy is more dependable, and there is less risk of failure or fatigue of the shaft 14 than in the prior art. The objective head 34 can be located inside the front end of the tube 40; the same tube which extends along the rest of the shaft and not merely along the active deflection assembly as in the prior art.

Tubes of superelastic alloy can be easily purchased from manufacturers at the present time. The tubes are presently manufactured with a uniform wall thickness, but it may be possible to vary the wall thickness along the length of the tube for different stiffness properties. However, tubes of superelastic alloy presently sold by manufacturers do not have slots in them. In order to manufacture the endoscope 10 the slots 46 need to be made into the tube of superelastic alloy. The tube can be purchased in precut lengths. One method of forming the slots 46 can comprise a laser cutting device. A laser of the device could cut the slots 46 into the solid tube with the device moving the tube and/or the laser. In a preferred embodiment, a programmable computer controller is used to control the device to form the slots 46 in the desired pattern(s) along the length of the tube. Thus, the pattern(s) can be selected or altered by appropriate computer programming to provide tubes with different slot patterns. These different types of tubes can be used to form endoscopes with different shaft properties, such as different stiffness properties along their lengths and different active deflection capabilities at their active deflection sections (one-way, two-way, four-way, etc.). In an alternate method wire electrical discharge machining (EDM) can be used to form the slots. However, any suitable method could be used to form the slots.

One of the advantages of the present invention is the ability to manufacture endoscopes with different shaft properties by providing tubes with different slot patterns, such as by merely having more or less slots 46 in the tube 40. With this advantage a user can select an endoscope with a desired shaft stiffness configuration from a plurality of endoscopes with the endoscopes otherwise being virtually identical. The manufacturer could also custom build an endoscope with a desired shaft stiffness configuration for a user by merely reprogramming the slot forming device with an appropriate slot pattern. The present invention also allows a shaft to be disassembled and more slots added to the tube 40 to change shaft properties if desired.

Figure 8:
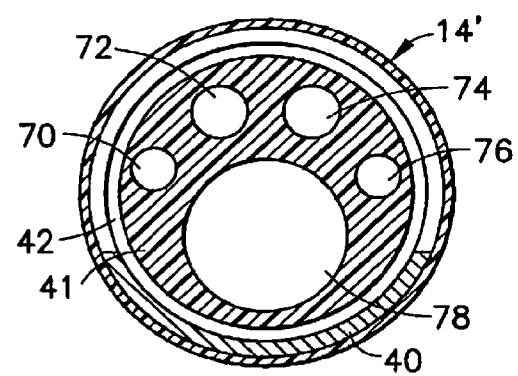
FIG. 8 is a cross-sectional view of an alternate embodiment of a shaft.
Figure 6A:
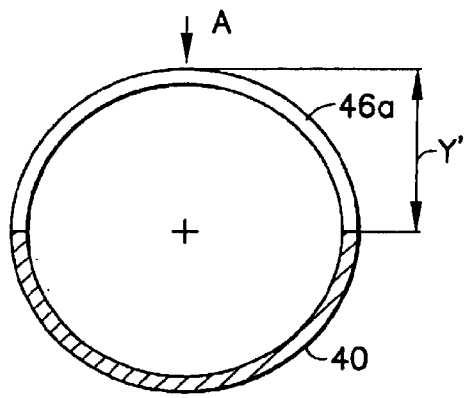
FIGS. 6A–6D are cross-sectional views of the third section of the tube shown in FIG. 3 showing the four different slot directions into the tube.
Figure 6C:
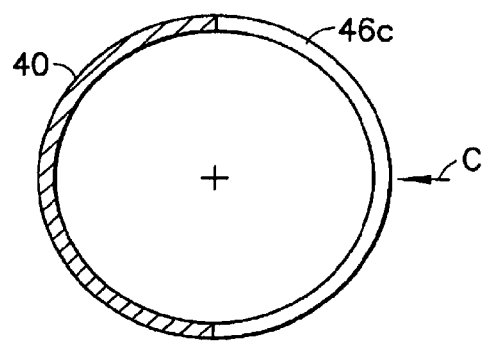
Figure 6B:
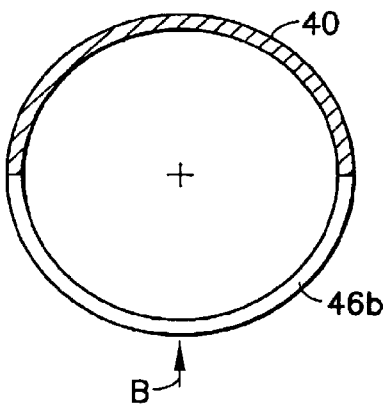
Figure 6D:
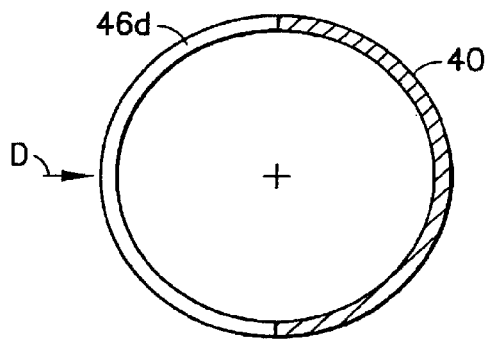
Figure 7A:
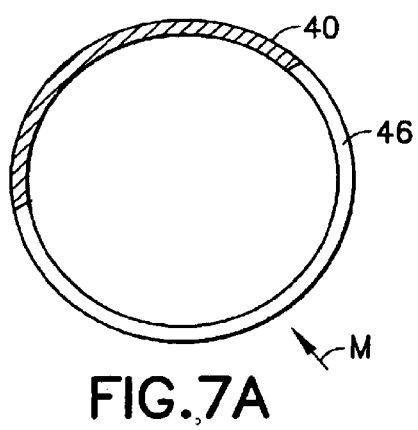
FIGS. 7A–7E are cross-sectional views of another alternate embodiment of a tube incorporating features of the present invention.
Figure 7B:
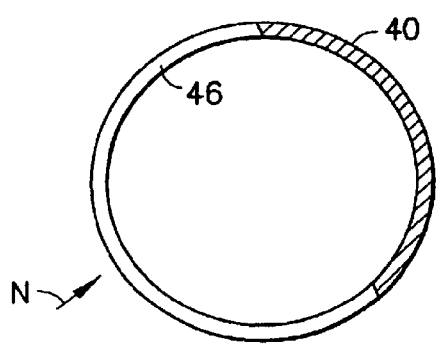
Figure 7D:
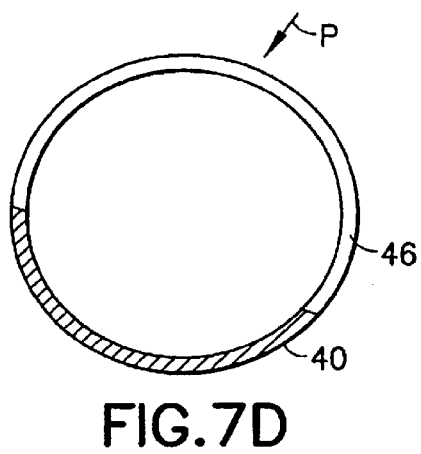
Figure 7C:
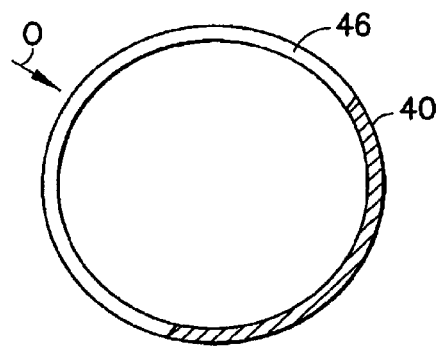
Figure 7E:
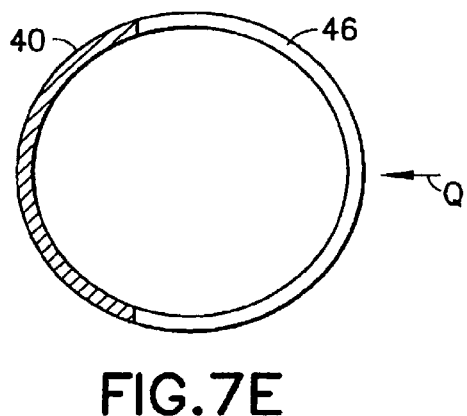

Endoscopes need to be cleaned after their use. One method of cleaning involves gas sterilization and pressure reduction. A problem with gas sterilization is that pressure inside the shaft pushes outward when pressure outside the shaft is reduced. With endoscopes having vent valves, this is usually not a problem. However, vent valves increase the cost of the endoscope and, if a user forgets to open the vent valve during cleaning, the shaft cover can burst. There are endoscopes that do not have vent valves. Instead, they have reinforced covers. A reinforced cover, as mentioned in the patent application identified above, can overcome this burst problem. Another way to overcome this problem is to provide a thin wall strengthening tube inside the tube 40. Referring also to FIG. 8, another way to overcome this problem is to provide the shaft 14' with a multi-lumen tube 41 inside the area 42 of the tube 40. The multi-lumen tube 41 can be comprised of a flexible polymer material and includes channels 70, 72, 74, 76 for the deflection control cables and fiber optics, as well as channel 78 which forms a working channel. The tube could also be a single lumen tube, such as the thin wall tube mentioned above.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An endoscope comprising:

a control section; and a shaft extending from the control section, the shaft comprising a generally tube shaped frame member;

wherein the shaft comprises a substantially uniform outer dimension along substantially an entire length of the shaft, and wherein the tube shaped frame member provides the shaft with at least two sections along the length of the shaft having two different stiffness properties, wherein an offset pattern of staggered slots is formed in the frame member to provide the different stiffness properties, wherein the frame member comprises a tube wall defining a center channel, wherein the tube wall has a substantially uniform tube wall thickness and a substantially uniform outer diameter, wherein the slots extend into the tube wall a distance about two-thirds or less than the outer diameter of the tube wall, and wherein the endoscope further comprises active deflection control wires and wire sheaths connected to the control section, wherein the wire sheaths each comprise an elongate solid tube made of superelastic alloy material.

2. An endoscope as in claim 1 wherein the frame member comprises a first section with a first pattern of slots therein and a second section with a second pattern of slots therein.

3. An endoscope as in claim 2 wherein the first pattern comprises a first spacing between the slots and the slots having a first slot width, and the second pattern comprises a second different spacing between the slots and a second different slot width.

4. An endoscope as in claim 2 wherein the first pattern comprises the slots extending into the frame member in a first repeating pattern of different directions and the second pattern comprising the slots extending into the frame member in a second repeating pattern of different directions which are at least partially different from the first repeating pattern of directions.

5. An endoscope as in claim 2 wherein the first pattern comprises the slots having a first depth and the second pattern comprises the slots having a second different depth.

6. The endoscope shaft of claim 1 wherein each slot depth extends beyond a radius of the frame member.

7. An endoscope as in claim 1 wherein the frame member comprises a center axis along the center channel, wherein the slots extend into the tube wall generally perpendicular to the center axis, and wherein the tube wall does not have holes parallel to the center axis such that the control wires extend through the center channel and not through the tube wall.

8. An endoscope as in claim 1 wherein the shaft further comprises at least one other flexible frame member connected in series to the tube shaped frame member to form a frame of the shaft.

9. In an endoscope comprising a shaft and an image transferring system passing through the shaft, the improvement comprising:

the shaft having a frame comprising a first frame member having a generally tubular shape connected to a second bendable frame member having a generally tubular shape, wherein the second member is connected in series with the first member, wherein the second frame member is comprised of superelastic material with a plurality of slots in different directions into lateral sides of the second member, wherein the second frame member comprises a tube shape with a uniform outer diameter, a center channel and a tube wall, wherein the slots extend into the second frame member a distance between one-half and two-thirds the outer diameter, wherein the slots on one of the lateral sides of the second frame member are offset from and interleaved with the slots on an opposite one of the lateral sides of the second frame member, and wherein the shaft comprises an active deflection section, wherein the second frame member is located in only the active deflection section, and wherein the endoscope further comprises an active deflection system comprising a pull wire and a wire sheath, the wire sheath comprising an elongate solid sheath tube made of superelastic alloy material loaded in compression by tension on the pull wire, and wherein the pull wire extends along a channel inside the sheath tube.

10. An endoscope as in claim 9 wherein the second frame member comprises a center axis along the center channel, wherein the slots extend into the tube generally perpendicular to the center axis, and wherein the tube wall does not have holes parallel to the center axis such that the pull wire extends through the center channel and not through the tube wall.

11. In an endoscope comprising a control section and a shaft extending from the control section, the improvement comprising:

the shaft having a frame with a one-piece tube, wherein the tube comprises a superelastic alloy and a plurality of slots into the tube along at least one section of the tube, wherein the slots into a first side of the tube are offset from and interleaved with the slots on an opposed second side of the tube, wherein the slots have a depth into the tube a distance of about two-thirds or less than an outer diameter of the tube, wherein the tube comprises a uniform wall thickness and a uniform outer diameter, and wherein superelastic properties of the superelastic alloy allow the tube to bend proximate the slots without substantial permanent deformation of the tube and the superelastic alloy Provides the shaft with adequate column strength, flexibility, and torque resistance to be inserted into a patient's body, wherein the tube comprises a center channel along a center axis, wherein the slots extend into the tube generally perpendicular to the center axis, and wherein the tube has a tube wall surrounding the center axis and having the uniform wall thickness which does not have holes parallel to the center axis such that control wires from the control section extend through the center channel and not through the tube wall, and wherein the endoscope further comprises wire sheaths surrounding the control wires, wherein the wire sheaths each comprise an elongate solid sheath tube made of superelastic alloy material loaded in compression by tension on the control wires.

12. In an endoscope comprising a shaft, an imaging and illumination system passing through the shaft, and a deflection control system passing through the shaft, the improvement comprising:

the shaft includes a frame comprising a tube of superelastic material with slots into the tube along opposite sides of the tube, wherein the tube comprises a center channel surrounded by a tube wall, the tube wall comprising a uniform outer diameter and a uniform wall thickness, wherein the slots extend into the tube in at least two different directions perpendicular to a center axis of the tube and the slots on opposed sides of the tube are offset from one another, and wherein, except for the center channel, the tube wall does not comprise any longitudinal holes parallel to its center axis such that portions of the deflection control system pass through the center channel and not through the tube wall, wherein the slots extend into the tube a distance less than or equal to two-thirds the outer diameter of the tube, and wherein the slots on the opposed sides are interleaved with each other, wherein the deflection control system comprises a pull wire and a wire sheath, the wire sheath comprising an elongate solid sheath tube made of superelastic alloy material loaded in compression by tension on the pull wire, and wherein the pull wire extends along a channel inside the sheath tube.

* * * * *